United States Patent [19]

Ellis, Jr. et al.

[11] Patent Number: 5,120,882
[45] Date of Patent: Jun. 9, 1992

[54] NITRATED METALLOPORPHYRINS AS CATALYSTS FOR ALKANE OXIDATION

[75] Inventors: Paul E. Ellis, Jr., Downingtown; James E. Lyons, Wallingford, both of Pa.

[73] Assignee: Sun Refining and Marketing Company, Philadelphia, Pa.

[21] Appl. No.: 758,147

[22] Filed: Sep. 12, 1991

[51] Int. Cl.[5] .................... C07C 29/50; C07C 31/12
[52] U.S. Cl. .................... 568/910; 568/910.5
[58] Field of Search ................ 568/910, 910.5

[56] References Cited

U.S. PATENT DOCUMENTS

| | | | |
|---|---|---|---|
| 3,816,548 | 6/1974 | Williams et al. | 568/910 |
| 4,028,423 | 6/1977 | Brownstein et al. | 568/910 |
| 4,459,427 | 7/1984 | Middleton et al. | 568/910 |
| 4,895,680 | 1/1990 | Ellis et al. | 568/910 |
| 4,895,682 | 1/1990 | Ellis et al. | 568/910.5 |
| 4,900,871 | 2/1990 | Ellis et al. | 568/910.5 |
| 4,912,266 | 3/1990 | Sanderson et al. | 568/910 |
| 4,912,269 | 3/1990 | Sanderson et al. | 568/910 |
| 4,922,034 | 5/1990 | Sanderson et al. | 568/910 |
| 4,978,799 | 12/1990 | Sanderson et al. | 568/910 |

Primary Examiner—J. E. Evans
Attorney, Agent, or Firm—Q. Todd Dickinson; Donald R. Johnson

[57] ABSTRACT

Alkanes are oxidized by contact with oxygen-containing gas in the presence as catalyst of a metalloporphyrin in which hydrogen atoms in the porphyrin ring have been replaced with one or more nitro groups. Hydrogen atoms in the porphyrin ring may also be substituted with halogen atoms.

8 Claims, No Drawings

NITRATED METALLOPORPHYRINS AS CATALYSTS FOR ALKANE OXIDATION

BACKGROUND OF THE INVENTION

This invention relates to oxidation of alkanes using metalloporphyrins as catalysts, and more particularly to such processes in which nitro groups have been substituted for hydrogen in the porphyrin ligand.

The use of metalloporphyrins as catalysts for the oxidation of hydrocarbons with air in the liquid phase has been shown in our U.S. Pat. Nos. 4,895,680 and 4,895,682 with the further finding that halogenation of the porphyrin ring led to even more active and stable catalysts (our U.S. Pat. Nos. 4,900,871 and 4,895,682 and pending application Ser. No. 568,118 filed Aug. 16, 1990). Since these discoveries we have been able to correlate increased electron withdrawal from halogenation of the porphyrin ring to increased catalytic air oxidation activity. J. E. Lyons and P. E. Ellis, Jr., Catalysis Letters 8, 45 (1991).

It is also known that other functional groups besides halogens can lead to electron withdrawal in porphyrins. For example, L. C. Gong and D. Dolphin in Can. J. Chem., 63, 401 (1985) found that successive nitration at the meso positions of Zn(octaethylporphine) eventually giving Zn(mesotetranitrooctaethylporphine) led to more easily reduced porphyrins, evidence for electron withdrawal from the ring. Other workers such as Catalano, et.al. in J. Chem. Soc., 1535 (1984) have been able to nitrate the beta or pyrrolic positions in various metal tetraphenylporphyrins.

DESCRIPTION OF THE INVENTION

We have now found that nitrated metalloporphyrins and nitrated/halogenated metalloporphyrins have utility a catalysts for the oxidation with oxygen-containing gas of alkanes such as methane, ethane, propane, butanes and the like.

The process of the invention comprises contacting alkane with oxygen-containing gas in the presence of a metalloporphyrin in which 12.5 to 100 percent of the hydrogen atoms in the porphyrin ring have been replaced with nitro groups.

Preferably, the metal in the catalyst is selected from the group consisting of iron, chromium, manganese, ruthenium, cobalt or copper. Other metals known for making metalloporphyrins may be used, but in general such other metalloporphyrins are less active than metalloporphyrins containing the preferred metals above.

In one embodiment of the invention, the metalloporphyrin is substituted both with nitro groups and with halogen atoms. In such cases, preferably, 4 to 28 percent of the hydrogen atoms in the porphyrin ring have been replaced with nitro groups and 0 to 72 percent of the hydrogen atoms in the porphyrin ring have been replaced with halogen atoms. For example, in a porphyrin substituted with 20 fluorine atoms and 8 nitro groups, about 28 percent of the hydrogen atoms have been replaced with nitro groups and about 72 percent of the hydrogen atoms have been replaced with halogen atoms.

In one embodiment, 1 to 8 of the pyrrolic hydrogens in the porphyrin ring have been replaced with nitro groups. In a further embodiment, remaining hydrogens in the porphyrin ring have been replaced with halogen.

Preferably all of the hydrogen atoms have been replaced either with nitro groups or halogen atoms, but this is not essential.

Specific catalysts useful according to the invention include nitrated meso-perfluorinatedalkylporphyrin, nitrated iron tetrakispentafluorylphenylporphyrin and metallomesotetranitroporphine.

The catalysts used in the invention are particularly effective in the oxidation of alkanes and alkenes, including cycloalkanes and cycloalkenes, substituted alkanes and alkenes and the like. The starting materials include straight and branched-chain compounds having from about 1 to 2 carbon atoms, preferably 1 to 10 carbon atoms, such as methane, ethane, propane, n-butane, isobutane, n-pentane, n-hexane, 2-methylpentane, 3-methylpentane, heptane, 2-methylheptane 3-methylheptane, the corresponding alkene forms, and the like., as well as cycloalkanes and cycloalkenes having from about 5 to 20 carbon atoms, preferably 5 to 10 carbon atoms, such as cyclopentane, cyclohexane, cycloheptane, cyclooctane, the corresponding alkene forms, and the like.

The oxidation, which may be carried out in a generally known manner, is desirably conducted in the liquid phase, although this is not critical, using such organic solvents as benzene, acetic acid, acetonitrile, methyl acetate, or like solvents which are inert to the conditions of the reactions, or in a neat solution of the hydrocarbon if it is liquid, and under pressures ranging from about 15 to 1500 psig, preferably 30 to 750 psig, at temperature of from about 25 to 250o C., more preferably 70 to 180o C Depending upon whether the hydrocarbon to be oxidized is a solid, liquid or gas, it is dissolved in or bubbled through the solvent, together with air or oxygen, in the presence of the catalyst used according to the invention, for periods of time sufficient to yield the desired oxidation product, generally from about 0.5 to 100 hours, and more preferably from 1 to 10 hours.

The choice of solvent, while not critical, can have an effect on the rates and selectivities obtained and should be carefully selected in order to optimize the desired results. For example, it has been found that solvents such as acetonitrile and acetic acid are often very effective for the oxidation of alkanes to form oxygen-containing compounds, whereas reactions carried out in solvents such as methyl acetate or benzene may occur more slowly. Thus, by routine experimentation, the optimum solvent for the particular process can be readily determined.

The ratios of the various reactants may vary widely, and are not critical. For example, the amount of catalyst employed can range from about $10^{-6}$ to $10^{-3}$ moles per mole of hydrocarbon such as alkane, and more preferably from about $10^{-5}$ to $10^{-4}$ mole of catalyst per mole of hydrocarbon, although other amounts are not precluded; while the amount of oxygen relative to the hydrocarbon starting material may also vary widely, generally $10^{-2}$ to $10^2$ moles of oxygen per mole of hydrocarbon. Care should be taken since some of the ratios fall within explosive limits. As a group, the catalysts are almost always soluble unless used in large excess. Thus, as a rule, the reactions are generally carried out homogeneously.

The catalysts used in the process of the invention may be made by any suitable method, of which the following are examples.

EXAMPLE 1

Iron tetrakispentafluorophenylporphine chloride is reacted with nitrogen dioxide (1-8) equivalents in methylene chloride or benzene leading to varying amounts of nitration at the beta positions on the ring according to the severity of the reaction conditions. Beta-positions left unnitrated are subsequently halogenated using normal chlorination, bromination or fluorination techniques. The general structure for the products is:

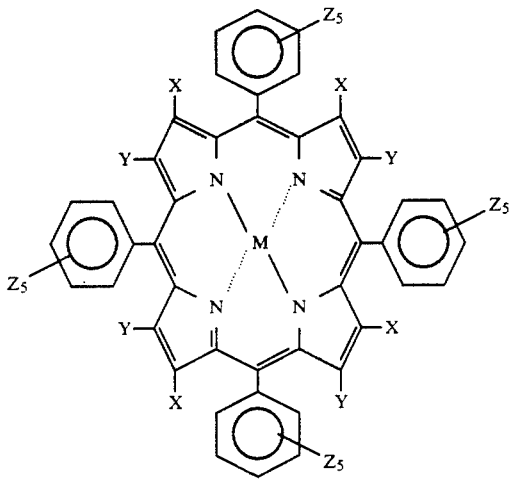

where M is Fe, Cr, Mn, Ru, Co or Cu, X is nitro, Y is nitro or Cl or Br or F and Z is H or Cl or Br or F.

EXAMPLE 2

Zn(porphine) is reacted with nitrogen dioxide in methylene chloride to produce Zn(mesotetranitroporphine). The zinc is removed by acid treatment and Fe or other transition metal, M, is inserted by the usual method of ferrous chloride or $MCl_2$ in dimethylformamide. The beta or pyrrolic hydrogens can be further nitrated or halogenated as desired. The general formula is:

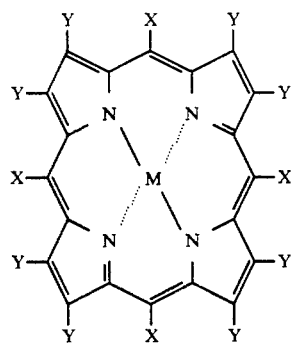

where M is Fe, Cr, Mn, Ru, Cu or Co, X is nitro, and Y is nitro, Cl, F, Br or any combination thereof.

EXAMPLE 3

Meso-perfluorinated alkyl porphyrins, made as disclosed in our copending application Serial No. 568,118 filed Aug. 16, 1990, the disclosure of which is herein incorporated by reference, can be nitrated in the beta or pyrrolic positions using nitrogen dioxide in methylene dichloride or nitric acid/sulfuric acid nitrating solutions. The general structure is:

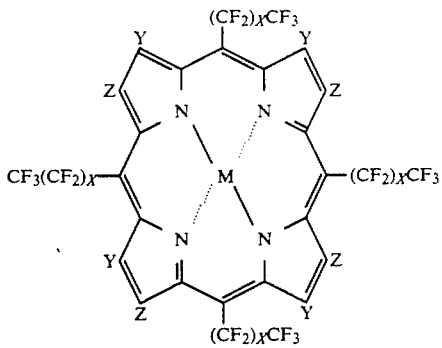

where M is Fe, Cr, Mn, Ru, Cu or Co, X is 0-6, and Y is nitro and Z is $NO_2$ or Cl or Br or F.

The invention will be further disclosed with reference to the following examples.

EXAMPLE 4

The catalyst prepared as described in Example 1 is used as a catalyst for the oxidation of isobutane to t-butyl alcohol in the following manner. Isobutane (6-7 grams) is dissolved in 25 ml of benzene containing the catalyst, and air is added to a pressure of 100 psi. Oxidation is carried out at a temperature of 60° C. for six hours. Gaseous and liquid products are analyzed by gas chromatography and mass spectrometry. Catalyst activity is expressed as "catalyst turnovers", i.e., moles of oxygen consumed/mole of catalyst. Selectivity is the moles of TBA per mole of liquid product. Higher numbers of catalyst turnovers and/or greater selectivity are obtained with the catalyst of the invention as compared with otherwise similar catalyst which has not been substituted with nitro groups. Similar results are obtained when the catalysts of Examples 2 and 3 above are used as alkane oxidation catalysts.

The invention claimed is:

1. Process for oxidation of alkanes which comprises contacting alkane with oxygen-containing gas in the presence of a metalloporphyrin in which hydrogen atoms in the porphyrin ring have been replaced with at least one nitro group.

2. Process according to claim 1 in which the metalloporphyrin contains iron, chromium, manganese, ruthenium, cobalt or copper.

3. Process according to claim 1 in which 1 to 8 of the pyrrolic hydrogen atoms in the porphyrin ring have bee replaced with nitro groups.

4. Process according to claim 3 in which remaining hydrogen atom in the porphyrin ring have been substituted with halogen atoms.

5. Process according to claim 4 in which 4 to 8 hydrogen atoms in the porphyrin ring have been replaced with nitro groups and in which 8 to 20 hydrogen atoms in the porphyrin ring have been replaced with halogen.

6. Process according to claim 1 in which the metalloporphyrin is a nitrated, mesoperfluorinated alkylporphyrin.

7. Process according to claim 1 in which the metalloporphyrin is a nitrated iron tetrakispentafluorophenylporphine.

8. Process according to claim 1 wherein the metalloporphyrin is a metallomesotetranitroporphine.

* * * * *

UNITED STATES PATENT AND TRADEMARK OFFICE
CERTIFICATE OF CORRECTION

PATENT NO. : 5,120,882
DATED : June 9, 1992
INVENTOR(S) : P. E. Ellis, Jr. and J. E. Lyons It is certified that error appears in the above-identified patent and that said Letters Patent is hereby corrected as shown below:

Column 1, after the title and before "Background of the Invention" insert the following as a separate paragraph:

"The Government of the United States of America has rights in this invention pursuant to Cooperative Agreement No. DE-FC21-90MC26029 awarded by the U. S. Department of Energy."

Signed and Sealed this

First Day of March, 1994

Attest:

BRUCE LEHMAN

*Attesting Officer*     Commissioner of Patents and Trademarks